(12) United States Patent
Schroeder et al.

(10) Patent No.: US 8,067,593 B2
(45) Date of Patent: Nov. 29, 2011

(54) PROCESS FOR PREPARING AMINOCROTONYLAMINO-SUBSTITUTED QUINAZOLINE DERIVATIVES

(75) Inventors: Juergen Schroeder, Mainz (DE); Georg Dziewas, Urbar (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/101,198

(22) Filed: May 5, 2011

(65) Prior Publication Data

US 2011/0207932 A1    Aug. 25, 2011

Related U.S. Application Data

(62) Division of application No. 12/162,037, filed on Sep. 22, 2008, now Pat. No. 7,960,546.

(60) Provisional application No. PCT/EP2007/050752, filed on Jan. 25, 2007, now Pat. No. 7,960,546.

(30) Foreign Application Priority Data

Jan. 26, 2006  (EP) ..................... 06100914

(51) Int. Cl.
C07D 239/94 (2006.01)
(52) U.S. Cl. ....................................... 544/293
(58) Field of Classification Search .................. 544/293
See application file for complete search history.

(56) References Cited

U.S. PATENT DOCUMENTS

| | | | |
|---|---|---|---|
| 7,019,012 B2 | 3/2006 | Himmelsbach et al. | |
| 7,220,750 B2 | 5/2007 | Himmelsbach et al. | |
| 7,223,749 B2 | 5/2007 | Himmelsbach et al. | |
| 7,846,936 B2 | 12/2010 | Hilberg et al. | |
| 7,960,546 B2 | 6/2011 | Schroeder et al. | |
| 2002/0169180 A1 | 11/2002 | Himmelsbach et al. | |
| 2002/0173509 A1 | 11/2002 | Himmelsbach et al. | |
| 2003/0225079 A1 | 12/2003 | Singer et al. | |
| 2005/0043233 A1 | 2/2005 | Stefanic et al. | |
| 2005/0085495 A1 | 4/2005 | Soyka et al. | |
| 2006/0058311 A1 | 3/2006 | Munzert et al. | |
| 2006/0100223 A1 | 5/2006 | Himmelsbach et al. | |
| 2007/0027170 A1 | 2/2007 | Soyka et al. | |
| 2007/0099918 A1 | 5/2007 | Singer et al. | |
| 2007/0185091 A1 | 8/2007 | Himmelsbach et al. | |
| 2008/0254040 A1 | 10/2008 | Stefanic et al. | |
| 2009/0238828 A1 | 9/2009 | Munzert et al. | |
| 2009/0306044 A1 | 12/2009 | Solca et al. | |
| 2009/0306101 A1 | 12/2009 | Solca et al. | |
| 2009/0306378 A1 | 12/2009 | Schroeder et al. | |
| 2009/0318480 A1 | 12/2009 | Solca | |
| 2010/0010023 A1 | 1/2010 | Himmelsbach et al. | |
| 2010/0069414 A1 | 3/2010 | Himmelsbach et al. | |
| 2010/0144639 A1 | 6/2010 | Singer et al. | |
| 2011/0039863 A1 | 2/2011 | Hilberg et al. | |
| 2011/0046168 A1 | 2/2011 | Himmelsbach et al. | |

FOREIGN PATENT DOCUMENTS

| | | |
|---|---|---|
| WO | 0078735 A1 | 12/2000 |
| WO | 0250043 A1 | 6/2002 |
| WO | 03094921 A2 | 11/2003 |
| WO | 2004074263 A1 | 9/2004 |
| WO | 2004096224 A2 | 11/2004 |
| WO | 2005037824 A2 | 4/2005 |
| WO | 2006018182 A1 | 2/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |

OTHER PUBLICATIONS

International Search Report for PCT/EP2007/050752 mailed Jul. 11, 2007.

*Primary Examiner* — James O Wilson
*Assistant Examiner* — Brian McDowell
(74) *Attorney, Agent, or Firm* — Michael P. Morris; Anthony P. Bottino

(57) ABSTRACT

The invention relates to an improved process for preparing aminocrotonylamino-substituted quinazoline derivatives of general formula (I)

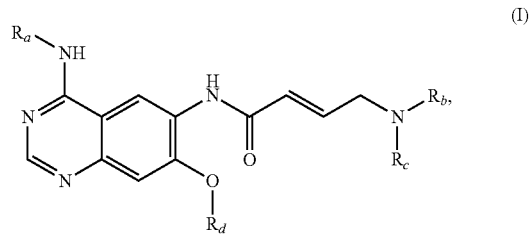

wherein the groups $R_a$, $R_b$, $R_c$ and $R_d$ have the meanings given in the claims, as well as sulphonyl derivatives of formula

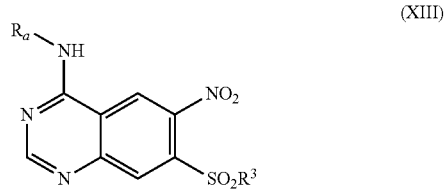

and the use thereof as synthesis components for preparing quinazolines of formula (I). The quinazoline derivatives of formula (I) are inhibitors of signal transduction mediated by tyrosinekinases and by the Epidermal Growth Factor-Receptor (EGF-R) and are therefore particularly suitable for the treatment of tumoral diseases.

4 Claims, No Drawings

PROCESS FOR PREPARING AMINOCROTONYLAMINO-SUBSTITUTED QUINAZOLINE DERIVATIVES

The invention relates to a process for preparing aminocrotonylamino-substituted quinazoline derivatives of general formula (I)

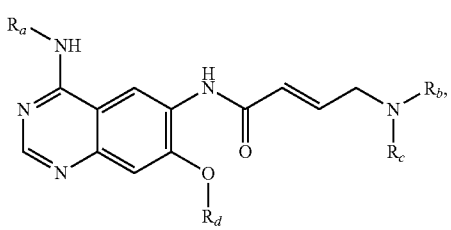

wherein the groups $R_a$, $R_b$, $R_c$ and $R_d$ have the meanings given in the claims and specification.

BACKGROUND TO THE INVENTION

Quinazoline derivatives of general formula (I) are known from WO 02/50043 and WO 04/074263, which describe compounds with valuable pharmacological properties, including in particular an inhibitory effect on signal transduction mediated by tyrosinekinases and an inhibitory effect on signal transduction mediated by Epidermal Growth Factor-Receptor (EGF-R). Therefore, compounds of this type are suitable for the treatment of diseases, particularly for the treatment of tumoral diseases, diseases of the lungs and airways and diseases of the gastro-intestinal tract and the bile ducts and gall bladder.

WO 2002/50043 discloses a method of production in which aminocrotonylamino-substituted quinazolines (I) are prepared in a one-pot reaction from the corresponding aniline component (II), bromocrotonic acid, oxalyl chloride and a secondary amine (see Diagram 1).

Diagram 1:

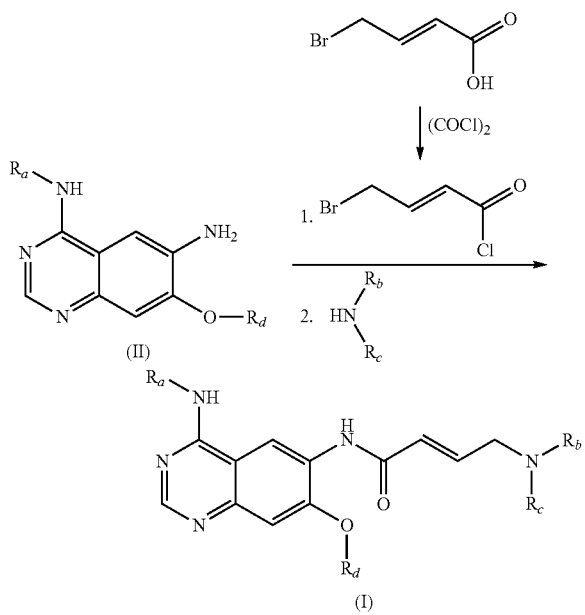

The process is not well suited to technical use on an industrial scale, as the yields obtained are at most 50% and as a rule laborious purification by column chromatography is needed. Moreover the educt bromocrotonic acid is not commercially available in large amounts and the corresponding methyl bromocrotonate is only available with a purity of about 80%.

WO 2005/037824 describes an alternative process for preparing aminocrotonylamino-substituted quinazoline derivatives of general formula (I) by Wittig-Horner-Emmons reaction of dialkyl-phosphonoacetamido-substituted quinazolines (III) with a 2-aminoacetaldehyde (IV) (Diagram 2), while instead of the aldehyde (IV) it is possible to use the corresponding hydrate or an acetal (e.g. the diethylacetal corresponding to (IV)), from which the aldehyde is liberated (beforehand or in situ).

Diagram 2:

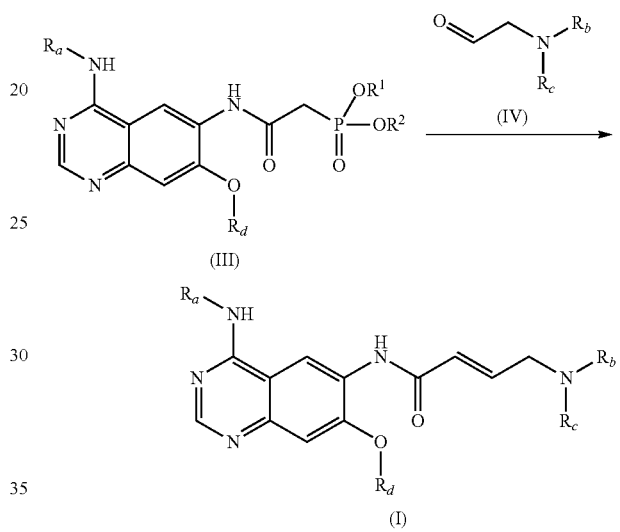

The educts of formula III may be obtained according to WO 2005/037824 as follows:

Diagram 3:

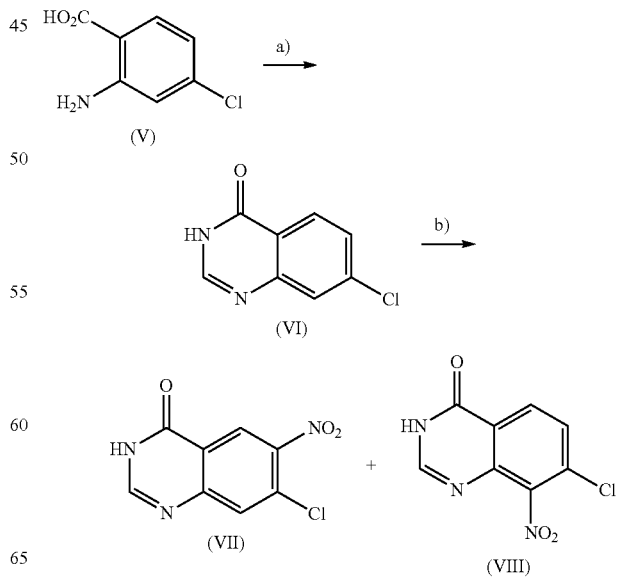

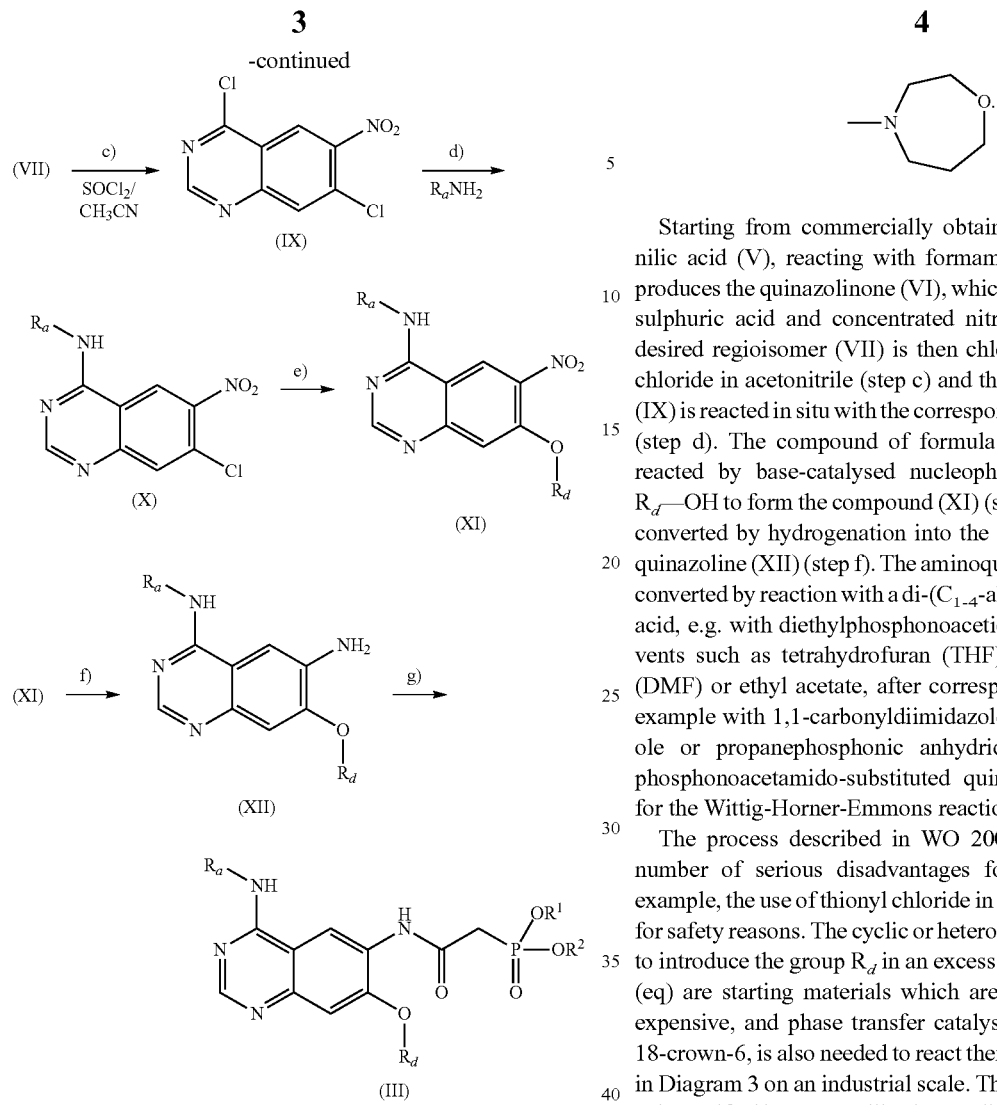

Starting from commercially obtainable 4-chloro-anthranilic acid (V), reacting with formamidine acetate (step a) produces the quinazolinone (VI), which is then nitrated using sulphuric acid and concentrated nitric acid (step b). The desired regioisomer (VII) is then chlorinated using thionyl chloride in acetonitrile (step c) and the chlorination product (IX) is reacted in situ with the corresponding amine $R_a$—$NH_2$ (step d). The compound of formula (X) thus obtained is reacted by base-catalysed nucleophilic substitution with $R_d$—OH to form the compound (XI) (step e), which is in turn converted by hydrogenation into the corresponding aminoquinazoline (XII) (step f). The aminoquinazoline (XII) is then converted by reaction with a di-($C_{1-4}$-alkyl)-phosphonoacetic acid, e.g. with diethylphosphonoacetic acid, in suitable solvents such as tetrahydrofuran (THF), dimethylformamide (DMF) or ethyl acetate, after corresponding activation, for example with 1,1-carbonyldiimidazole, 1,1-carbonylditriazole or propanephosphonic anhydride, into the dialkylphosphonoacetamido-substituted quinazoline (III) needed for the Wittig-Horner-Emmons reaction.

The process described in WO 2005/037824 also has a number of serious disadvantages for technical use. For example, the use of thionyl chloride in Step (c) is problematic for safety reasons. The cyclic or heterocyclic alcohols needed to introduce the group $R_d$ in an excess of about 2 equivalents (eq) are starting materials which are difficult to obtain or expensive, and phase transfer catalysis, for example using 18-crown-6, is also needed to react them according to step (e) in Diagram 3 on an industrial scale. The reaction product has to be purified by recrystallisation to eliminate the phase transfer catalyst. The hydrogenation of step (f) is carried out with the addition of acetic acid, if the educt contains a chlorine atom, so as to prevent the formation of dechlorinated by-products which are difficult to strip out. The addition of acetic acid causes traces of the nickel needed as catalyst to be dissolved, and this is then entrained into the final step and gives rise to a heavy metal problem which is unacceptable for pharmaceutical use. Moreover, the throughput of individual partial reactions is in need of improvement; for example the throughput in step (e) according to Diagram 3 is only 1/60 (1 kg of starting material require a reactor volume of 60 l).

In the light of the disadvantages of the known production method as described above, the problem of the present invention is to provide an improved method, suitable for synthesis on an industrial scale, which permits the safe preparation of aminocrotonylamino-substituted quinazoline derivatives (I) using easily obtainable starting materials of high purity and at a lower technical cost.

Both in the prior art described above and within the scope of the invention described hereinafter, the groups $R_a$, $R_b$, $R_c$, $R_d$, $R^1$ and $R^2$ have the following meanings:

$R_a$ denotes a benzyl, 1-phenylethyl or 3-chloro-4-fluorophenyl group, $R_b$ denotes a methyl, ethyl, isopropyl, cyclopropyl, 2-methoxyethyl, tetrahydrofuran-3-yl, tetrahydrofuran-2-ylmethyl, tetrahydrofuran-3-yl-methyl, tetrahydropyran-4-yl or tetrahydropyran-4-yl-methyl group, $R_c$ denotes a methyl, ethyl or 2-methoxyethyl group or $R_b$ and $R_c$ together with the nitrogen atom to which these groups are bound denote a morpholino or homomorpholino group optionally substituted by one or two $C_{1-3}$-alkyl groups, $R_d$ denotes a cyclopropylmethyl, cyclobutyl, cyclopentyl, tetrahydrofuran-3-yl, tetrahydrofuran-2-yl-methyl, tetrahydrofuran-3-yl-methyl, tetrahydropyran-4-yl or tetrahydropyran-4-yl-methyl group, and $R^1$ and $R^2$ each independently of one another denote a $C_{1-4}$-alkyl group, for example each denote an ethyl group.

By a homomorpholino group is meant the next highest ring-homologue of the morpholino group, namely the group of formula

DETAILED DESCRIPTION OF THE INVENTION

The problem stated above is solved according to the invention by the following process for preparing a compound of general formula

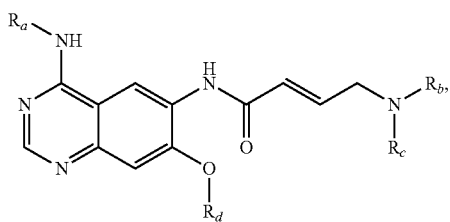

wherein $R_a$ to $R_d$ are as hereinbefore defined, comprising the following steps Embodiment A a) reacting 7-chloro-6-nitro-3H-quinazolin-4-one

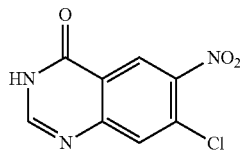

with a primary amine of formula $R_a$—$NH_2$ (XV), wherein $R_a$ denotes a benzyl, 1-phenylethyl or 3-chloro-4-fluorophenyl group, in the presence of $POCl_3$, b) converting the resulting compound of general formula

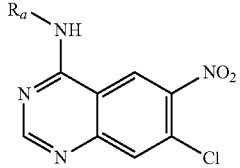

into the sulphonyl derivative of formula

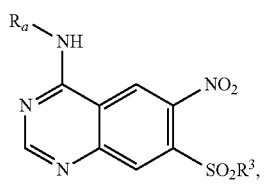

wherein $R^3$ denotes a $C_{1-4}$-alkyl group wherein the hydrogen atoms may be wholly or partly replaced by fluorine atoms, or a phenyl group optionally substituted by one to three substituents selected from $C_{1-3}$-alkyl groups, halogen atoms, particularly fluorine, chlorine or bromine atoms, cyano or nitro groups, while the substituents may be identical or different, and wherein $R_a$ in the two formulae (X) and (XIII) has the meanings given under a), c) converting the sulphonyl derivative of formula (XIII) into a compound of formula

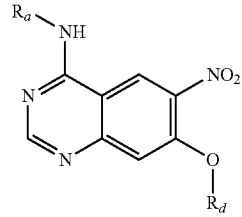

by reacting with an alcohol of formula $R_d$—OH (XVI) in the presence of a base, wherein $R_a$ has the meanings given under a) and $R_d$ denotes a cyclopropylmethyl, cyclobutyl, cyclopentyl, tetrahydrofuran-3-yl, tetrahydrofuran-2-yl-methyl, tetrahydrofuran-3-yl-methyl, tetrahydropyran-4-yl or tetrahydropyran-4-yl-methyl group, d) reducing the compound of formulae (XI) thus obtained to the amino derivative of formula

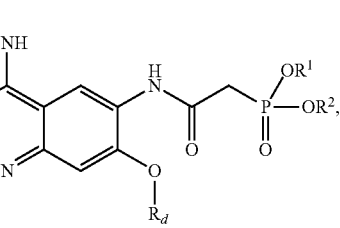

wherein $R_a$ has the meanings given under a) and $R_d$ has the meanings given under c), e) converting the amino derivatives of formula (XII) into the phosphonic ester of formula

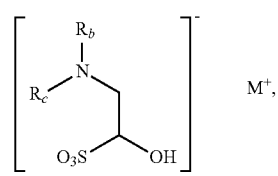

wherein $R_a$ has the meanings given under a), $R_d$ has the meanings given under c), and $R^1$ and $R^2$ each independently of one another denote a $C_{1-4}$-alkyl group, but preferably ethyl groups, f) reacting the resulting phosphonic ester of formula (III) with a hydrogen sulphite adduct of formula $$\left[ \begin{array}{c} R_b \\ | \\ R_c - N \\ | \\ O_3S \quad OH \end{array} \right]^- M^+, \quad (XIV)$$

wherein

M+ denotes a cation, for example the sodium ion, or a proton and $R_b$ denotes a methyl, ethyl, isopropyl, cyclopropyl, 2-methoxyethyl, tetrahydrofuran-3-yl, tetrahydrofuran-2-yl-methyl, tetrahydrofuran-3-yl-methyl, tetrahydropyran-4-yl or tetrahydropyran-4-yl-methyl group, $R_c$ denotes a methyl, ethyl or 2-methoxyethyl group or $R_b$ and $R_c$ together with the nitrogen atom to which these groups are bound represent a morpholino or homomorpholino group optionally substituted by one or two $C_{1-3}$-alkyl groups, in the manner of a Wittig-Horner-Emmons reaction.

In another aspect the invention relates to the sulphonyl derivatives of formula

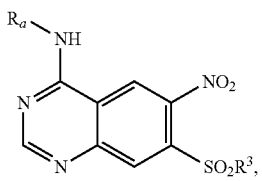

(XIII)

wherein $R_a$ denotes a benzyl, 1-phenylethyl or 3-chloro-4-fluorophenyl group and $R^3$ denotes a $C_{1-4}$-alkyl group wherein the hydrogen atoms may be wholly or partly replaced by fluorine atoms, or a phenyl group optionally substituted by one to three substituents selected from $C_{1-3}$-alkyl groups, halogen atoms, particularly fluorine, chlorine or bromine atoms, cyano or nitro groups, while the substituents may be identical or different, which are valuable synthesis components for preparing the pharmacologically active quinazoline derivatives of general formula (I).

For example $R^3$ in formula (XIII) may denote the p-toluenesulphonyl, p-bromo-benzenesulphonyl, phenyl, p-nitrobenzenesulphonyl, methylsulphonyl, trifluoromethylsulphonyl, nonafluorobutylsulphonyl or 2,2,2-trifluoroethanesulphonyl group.

The following are mentioned as particularly preferred compounds of formula (XIII):

(1) 4-(3-chloro-4-fluoro-phenylamino)-7-(4-methyl-phenylsulphonyl-)-6-nitro-quinazoline,
(2) 4-(3-chloro-4-fluoro-phenylamino)-7-(4-bromo-phenylsulphonyl)-6-nitro-quinazoline,
(3) 4-(3-chloro-4-fluoro-phenylamino)-7-(phenylsulphonyl)-6-nitro-quinazoline,
(4) 4-(3-chloro-4-fluoro-phenylamino)-7-(4-nitro-phenylsulphonyl)-6-nitro-quinazoline,
(5) 4-(3-chloro-4-fluoro-phenylamino)-7-(methylsulphonyl)-6-nitro-quinazoline,
(6) 4-(3-chloro-4-fluoro-phenylamino)-7-(trifluoromethylsulphonyl)-6-nitro-quinazoline,
(7) 4-(3-chloro-4-fluoro-phenylamino)-7-(nonafluorobutylsulphonyl)-6-nitro-quinazoline,
(8) 4-(3-chloro-4-fluoro-phenylamino)-7-(2,2,2-trifluoroethanesulphonyl)-6-nitro-quinazoline
(9) 4-(benzylamino)-7-(4-methyl-phenylsulphonyl-)-6-nitro-quinazoline,
(10) 4-(benzylamino)-7-(4-bromo-phenylsulphonyl)-6-nitro-quinazoline,
(11) 4-(benzylamino)-7-(phenylsulphonyl)-6-nitro-quinazoline,
(12) 4-(benzylamino)-7-(4-nitro-phenylsulphonyl)-6-nitro-quinazoline,
(13) 4-(benzylamino)-7-(methylsulphonyl)-6-nitro-quinazoline,
(14) 4-(benzylamino)-7-(trifluoromethylsulphonyl)-6-nitro-quinazoline,
(15) 4-(benzylamino)-7-(nonafluorobutylsulphonyl)-6-nitro-quinazoline,
(16) 4-(benzylamino)-7-(2,2,2-trifluoroethanesulphonyl)-6-nitro-quinazoline,
(17) 4-(1-phenylethylamino)-7-(4-methyl-phenylsulphonyl-)-6-nitro-quinazoline,
(18) 4-(1-phenylethylamino)-7-(4-bromo-phenylsulphonyl)-6-nitro-quinazoline,
(19) 4-(1-phenylethylamino)-7-(phenylsulphonyl)-6-nitro-quinazoline,
(20) 4-(1-phenylethylamino)-7-(4-nitro-phenylsulphonyl)-6-nitro-quinazoline,
(21) 4-(1-phenylethylamino)-7-(methylsulphonyl)-6-nitro-quinazoline,
(22) 4-(1-phenylethylamino)-7-(trifluoromethylsulphonyl)-6-nitro-quinazoline,
(23) 4-(1-phenylethylamino)-7-(nonafluorobutylsulphonyl)-6-nitro-quinazoline and
(24) 4-(1-phenylethylamino)-7-(2,2,2-trifluoroethanesulphonyl)-6-nitro-quinazoline.

The educts used in the process according to the invention and not described in more detail are either known from the literature or may be prepared from precursors known from the literature by simple analogous methods. For example, the sodium hydrogen sulphite adduct of formula (XIV) may be obtained from the corresponding acetal by liberating the corresponding aldehyde in hydrochloric acid solution and subsequent precipitation by the addition of $NaHSO_3$ solution. The diethylacetal may be prepared from the corresponding aldehyde by conventional methods.

Specifically, the invention described in embodiment A has the following partial aspects B, C and D:

B) Preparation of the Synthesis Component of Formula

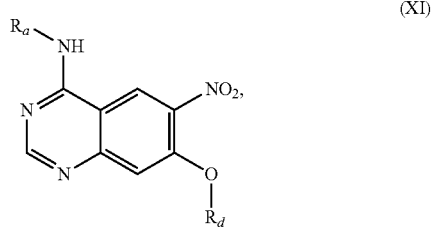

(XI)

wherein $R_a$ denotes a benzyl, 1-phenylethyl or 3-chloro-4-fluorophenyl group and $R_d$ denotes a cyclopropylmethyl, cyclobutyl, cyclopentyl, tetrahydrofuran-3-yl, tetrahydrofuran-2-yl-methyl, tetrahydrofuran-3-yl-methyl, tetrahydropyran-4-yl or tetrahydropyran-4-yl-methyl group, by a) reacting 7-chloro-6-nitro-3H-quinazolin-4-one

(VII)

with a primary amine of formula R$_a$—NH$_2$ (XV), wherein R$_a$ denotes a benzyl, 1-phenylethyl or 3-chloro-4-fluorophenyl group, in the presence of POCl$_3$, b) converting the resulting compound of general formula

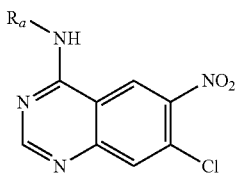
(X)

into the sulphonyl derivative of formula

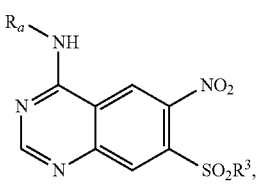
(XIII)

wherein

R$^3$ denotes a C$_{1-4}$-alkyl group wherein the hydrogen atoms may be wholly or partly replaced by fluorine atoms, or a phenyl group optionally substituted by one to three substituents selected from C$_{1-3}$-alkyl groups, halogen atoms, particularly fluorine, chlorine or bromine atoms, cyano or nitro groups, wherein the substituents may be identical or different, and wherein R$_a$ in the two formulae (X) and (XIII) has the meanings given under a), c) converting the sulphonyl derivative of formula (XIII) into a compound of formula

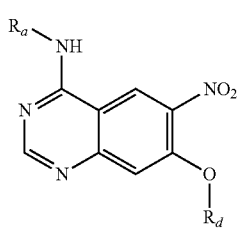
(XI)

by reacting with an alcohol of formula R$_d$—OH (XVI) in the presence of a base, wherein R$_a$ has the meanings given under a) and R$_d$ denotes a cyclopropylmethyl, cyclobutyl, cyclopentyl, tetrahydrofuran-3-yl, tetrahydrofuran-2-yl-methyl, tetrahydrofuran-3-yl-methyl, tetrahydropyran-4-yl or tetrahydropyran-4-yl-methyl group.

C) Preparing the Synthesis Component of Formula

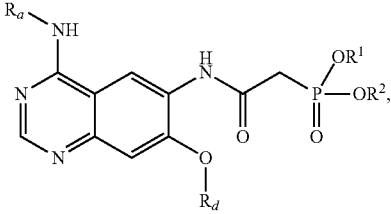
(III)

wherein

R$_a$ denotes a benzyl, 1-phenylethyl or 3-chloro-4-fluorophenyl group,

R$_d$ denotes a cyclopropylmethoxy, cyclobutyloxy, cyclopentyloxy, tetrahydrofuran-3-yl-oxy, tetrahydrofuran-2-yl-methoxy, tetrahydrofuran-3-yl-methoxy, tetrahydro-pyran-4-yl-oxy or tetrahydropyran-4-yl-methoxy group, and R$^1$ and R$^2$ each independently of one another denote a C$_{1-4}$-alkyl group, by preparing the synthesis component of formula

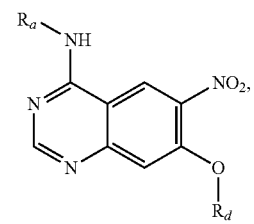
(XI)

wherein

R$_a$ denotes a benzyl, 1-phenylethyl or 3-chloro-4-fluorophenyl group and

R$_d$ denotes a cyclopropylmethyl, cyclobutyl, cyclopentyl, tetrahydrofuran-3-yl, tetrahydrofuran-2-yl-methyl, tetrahydrofuran-3-yl-methyl, tetrahydropyran-4-yl or tetrahydropyran-4-yl-methyl group, according to the process described under B) and subsequently d) reducing the compound of formulae (XI) thus obtained to the amino derivative of formula

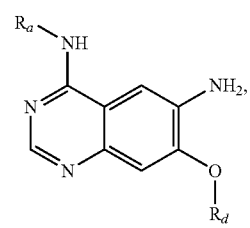
(XII)

wherein

R$_a$ denotes a benzyl, 1-phenylethyl or 3-chloro-4-fluorophenyl group and $R_d$ denotes a cyclopropylmethyl, cyclobutyl, cyclopentyl, tetrahydrofuran-3-yl, tetrahydrofuran-2-yl-methyl, tetrahydrofuran-3-yl-methyl, tetrahydropyran-4-yl or tetrahydropyran-4-yl-methyl group, and e) converting the amino derivatives of formula (XII) into the phosphonic ester of formula

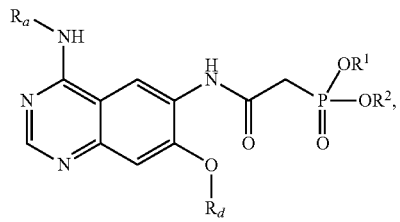

(III)

wherein $R_a$ and $R_d$ have the meanings given under d), and $R^1$ and $R^2$ each independently of one another denote a $C_{1-4}$-alkyl group.

D) Preparing a Compound of General Formula

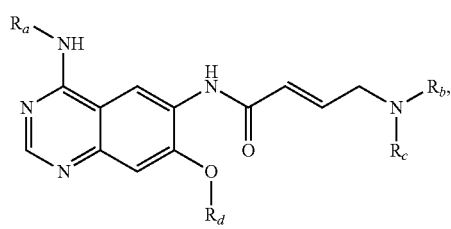

(I)

wherein $R_a$ denotes a benzyl, 1-phenylethyl or 3-chloro-4-fluorophenyl group, $R_b$ denotes a methyl, ethyl, isopropyl, cyclopropyl, 2-methoxyethyl, tetrahydrofuran-3-yl, tetrahydrofuran-2-yl-methyl, tetrahydrofuran-3-yl-methyl, tetrahydropyran-4-yl or tetrahydropyran-4-yl-methyl group, $R_c$ denotes a methyl, ethyl or 2-methoxyethyl group or $R_b$ and $R_c$ together with the nitrogen atom to which these groups are bound denote a morpholino or homomorpholino group optionally substituted by one or two $C_{1-3}$-alkyl groups and $R_d$ denotes a cyclopropylmethyl, cyclobutyl, cyclopentyl, tetrahydrofuran-3-yl, tetrahydrofuran-2-yl-methyl, tetrahydrofuran-3-yl-methyl, tetrahydropyran-4-yl or tetrahydropyran-4-yl-methyl group, by f) reacting a phosphonic ester of formula

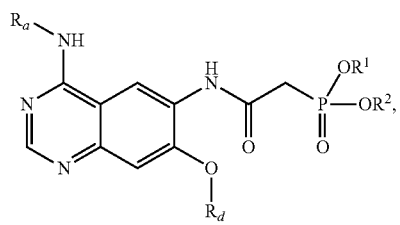

(III)

wherein $R_a$ denotes a benzyl, 1-phenylethyl or 3-chloro-4-fluorophenyl group, $R_d$ denotes a cyclopropylmethyl, cyclobutyl, cyclopentyl, tetrahydrofuran-3-yl, tetrahydrofuran-2-yl-methyl, tetrahydrofuran-3-yl-methyl, tetrahydropyran-4-yl or tetrahydropyran-4-yl-methyl group and $R^1$ and $R^2$ each independently of one another denote a $C_{1-4}$-alkyl group, with the hydrogen sulphite adduct of formula

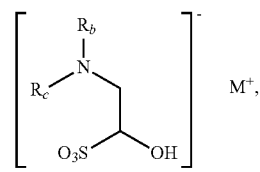

(XIV)

wherein $M^+$ denotes a cation, for example the sodium ion or a proton, $R_b$ denotes a methyl, ethyl, isopropyl, cyclopropyl, 2-methoxyethyl, tetrahydrofuran-3-yl, tetrahydrofuran-2-yl-methyl, tetrahydrofuran-3-yl-methyl, tetrahydropyran-4-yl or tetrahydropyran-4-yl-methyl group, $R_c$ denotes a methyl, ethyl or 2-methoxyethyl group or $R_b$ and $R_c$ together with the nitrogen atom to which these groups are bound denote a morpholino or homomorpholino group optionally substituted by one or two $C_{1-3}$-alkyl groups, in the manner of a Wittig-Horner-Emmons reaction.

The reaction (a) of 7-chloro-6-nitro-3H-quinazolin-4-one (VII) with a primary amine of formula (XV) for preparing a compound of formula (X) is carried out in a suitable solvent, for example in acetonitrile, dioxane, THF, or mixtures thereof, e.g. in a mixture of acetonitrile, dioxane and in the presence of 1-2 equivalents $POCl_3$, at a temperature of 50 to 80° C.

The conversion (b) of a compound of formula (X) into the sulphonyl derivative of formula (XIII) is carried out in a suitable solvent, for example in acetonitrile, dioxane, THF, DMF, dimethylacetamide (DMA), N-methylpyrrolidone (NMP) or mixtures thereof, e.g. in a mixture of DMF and NMP by the addition of 1 to 2 equivalents of a corresponding sulphinic acid salt, for example the sodium salt of benzenesulphinic acid, at a temperature between 50° C. and the boiling temperature of the solvent used, preferably at a temperature between 80 and 100° C.

The conversion (c) of the sulphonyl derivative of formula (XIII) into a compound of formula (XI) is carried out in a suitable solvent, for example in acetonitrile, dioxane, THF, DMF, DMA, diglyme, tert-butanol or mixtures thereof, by the addition of 1 to 1.5 equivalents of an alcohol of formula $R_d$—OH (XVI) and subsequent batchwise addition of 2 to 4 equivalents of a strong base, for example powdered NaOH, KOH or LiOH, or potassium-tert.-butoxide, sodium-tert.-butoxide, lithium-tert.-butoxide, potassium-tert.-amylate, sodium-tert.-amylate or lithium-tert.-amylate as a solid or by dropwise addition of a solution of these bases in tert. butanol, THF or DMF, at a temperature between 0 and 100° C., preferably between 10 and 50° C., initially choosing a low temperature and raising the temperature after the addition of the base to complete the reaction.

The reduction (d) of a compound of formula (XI) to the amino derivative of formula (XII) is preferably carried out by catalytic hydrogenation with hydrogen in the presence of a catalyst such as Raney nickel, palladium/charcoal or platinum in a solvent such as methanol, ethanol, ethyl acetate, DMF, DMA, NMP, DMF/acetone or DMF/methanol, optionally with the addition of an acid such as acetic acid or an acid salt at temperatures between 0 and 100° C., for example at temperatures between 0 and 80° C., but preferably at a temperature between 20 and 50° C., and under a hydrogen pressure of 1 to 10 bar, for example 1 to 7 bar, but preferably at a pressure of from 3 to 5 bar.

The conversion (e) of the amino derivative of formula (XII) into the phosphonic ester of formula (III) is carried out by reacting with 1.0-2.0 equivalents of a di-($C_{1-4}$-alkyl)-phosphonoacetic acid, preferably with diethylphosphonoacetic acid, in a suitable solvent such as THF, DMF, toluene, ethyl acetate, methyl-tert.-butylether (MTBE) or mixtures thereof, e.g. in MTBE/THF, after corresponding activation at temperatures between 0° C. and 100° C. The activation may be carried out using any of the current methods of amide linking, i.e. for example with 1,1-carbonyldiimidazole, 1,1-carbonylditriazole, DCC (N,N-dicyclohexylcarbodiimide), EDC (N'-(dimethylaminopropyl)-N-ethylcarbodiimide), TBTU O-(benzotriazol-1-yl)-N,N,N',N'-tetramethyluronium tetrafluoroborate, thiazolidine-2-thione, or by conversion into the corresponding acid chloride, possibly using thionyl chloride or phosphorus oxychloride. Optionally the activation is carried out using organic bases such as triethylamine or pyridine, while DMAP (dimethylaminopyridine) may additionally be added.

The reaction (f) of the phosphonic ester of formula (III) with the hydrogen sulphite adduct of formula (XIV) is carried out in a suitable solvent such as methanol, ethanol, THF, DMF, toluene, ethyl acetate and acetonitrile or mixtures thereof or in a binary or ternary mixture with water, preferably in ethanol or ethanol/water, with the addition of a suitable base, e.g. sodium carbonate, lithium hydroxide, sodium hydroxide or potassium hydroxide, optionally with the addition of a stabilising salt such as lithium chloride, at a temperature of 0° C.-50° C., using 1-2 equivalents, preferably 1.2-1.6, e.g. 1.4 equivalents of the hydrogen sulphite adducts in aqueous solution.

Preferred embodiments of the process according to the invention with all the partial steps (a) to (f) as well as the partial aspects B, C and D relate to the preparation of compounds of formula (I), wherein $R_a$ denotes a 3-chloro-4-fluorophenyl group and $R_b$, $R_c$ and $R_d$ are defined as mentioned in embodiment A (embodiment F), or $R_b$ and $R^c$ in each case denote a methyl group and $R_a$ and $R_d$ are defined as mentioned in embodiment A (embodiment H), or $R_a$ denotes a 3-chloro-4-fluorophenyl group, $R_b$ and $R^c$ each denote a methyl group and $R_d$ are defined as mentioned in embodiment A (embodiment I), or $R_d$ denotes a tetrahydrofuran-3-yl or tetrahydropyran-4-yl group and $R_a$, $R_b$ and $R_c$ are defined as mentioned in embodiment A (embodiment J), or $R_a$ denotes a 3-chloro-4-fluorophenyl group, $R_b$ and $R^c$ in each case denote a methyl group and $R_d$ denotes a tetrahydrofuran-3-yl or tetrahydropyran-4-yl group (embodiment K), or $R_a$ denotes a 3-chloro-4-fluorophenyl group, $R_b$ and $R^c$ together with the nitrogen atom to which these groups are bound denotes a morpholine group and $R_d$ denotes a tetrahydrofuran-3-yl or tetrahydropyran-4-yl group (embodiment L), or $R_a$ denotes a 3-chloro-4-fluorophenyl group, $R_b$ and $R^c$ together with the nitrogen atom to which these groups are bound denotes a homomorpholine group and $R_d$ denotes a tetrahydrofuran-3-yl or tetrahydropyran-4-yl group (embodiment M), while $R_a$, $R_b$, $R_c$ and $R_d$ in partial steps (a) to (f), in each case corresponding to embodiments F to M, assume the meanings given therein.

The process according to the invention is used to particular advantage to prepare the compound

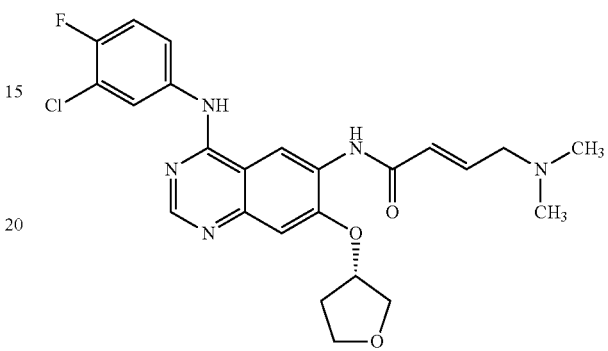

4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, or the corresponding R-enantiomer.

The aminocrotonylamino-substituted quinazoline derivatives of formula (I) obtained by the process according to the invention may subsequently be converted by known methods into the salts thereof, particularly into physiologically acceptable salts, for example into fumarates, tartrates or maleates. The conversion of the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline obtained according to the invention into the corresponding dimaleate is preferred, as described in WO 2005/037824.

The following Examples are intended to illustrate the invention in more detail:

EXAMPLE 1

4-(3-Chloro-4-fluoro-phenylamino)-7-chloro-6-nitro-quinazoline 20 g 7-chloro-6-nitro-3H-quinazolin-4-one are suspended in 80 ml acetonitrile and combined with 16.5 g phosphorus oxychloride. Then 10.8 g triethylamine are slowly added dropwise and the mixture is heated to about 80° C. After 5 hours a solution of 15.5 g 3-chloro-4-fluoroaniline in 100 ml dioxane is added dropwise and the mixture is stirred for another hour. Then 80 ml of water is added, the mixture is cooled to 20° C. and made slightly alkaline with KOH solution. The suspension is suction filtered, washed with water and ethanol and dried at 50° C. in vacuo.

Yield: 29.07 g (89.5% of theoretical/dioxane solvate) m.p.: 272-274° C.

EXAMPLE 2

4-(3-Chloro-4-fluoro-phenylamino)-7-(phenylsulphonyl)-6-nitro-quinazoline 500 g 4-(3-chloro-4-fluoro-phenylamino)-7-chloro-6-nitro-quinazoline and 302 g (1.3 eq) benzenesulphinic acid sodium salt are suspended at 20° C. in 1500 ml DMF, heated to 90° C. and kept for 6 h at this temperature. After cooling the reaction mixture the suspension is suction filtered and the residue is rinsed with 1.5 l methanol, 10 l water and 0.5 l methanol. The residue is dried at 50° C. for about 12 h under reduced pressure.

Yield: 631.2 g (86.2% of theoretical/DMF solvate). m.p.: 284-286° C.

EXAMPLE 3

4-[(3-Chloro-4-fluorophenyl)amino]-6-nitro-7-((S)-tetrahydrofuran-3-yloxy)-quinazoline 810 g of 4-(3-chloro-4-fluoro-phenylamino)-7-(phenyl-sulphonyl)-6-nitro-quinazoline and 175.5 g (S)-3-hydroxytetrahydrofuran (1.3 eq) are placed at 20° C. in 1.04 l tert-butanol and 198 ml DMF, 2556 g K-tert.-butoxide in THF (24%) (3.6 eq) are added dropwise at 20° C. and then stirred for 4 h at 25° C. After a further 2 h at 40° C. the mixture is heated to 45° C. for about 2 h. 2.8 l of water are added and then about 3 l solvent are distilled off under reduced pressure. 2.8 l water are added again and about 900 ml solvent are distilled off under reduced pressure. After the addition of 1.6 l methanol the mixture is cooled to 20° C. The suspension is suction filtered and rinsed with a mixture of 3.2 l water and 1.6 l methanol. The residue is dried overnight at 50° C. under reduced pressure.

Yield: 598.6 g (89.6% of theoretical). m.p.: 238-240° C.

EXAMPLE 4

4-[(3-Chloro-4-fluorophenyl)amino]-6-amino-7-((S)-tetrahydrofuran-3-yloxy)-quinazoline 100 g of 4-[(3-chloro-4-fluorophenyl)amino]-6-nitro-7-((S)-tetrahydrofuran-3-yloxy)-quinazoline are hydrogenated in 400 ml DMF in the presence of 33.1 g Raney nickel and 18.7 g ammonium chloride at 40° C., until the calculated amount of hydrogen has been taken up. The catalyst is filtered off and the filtrate is added dropwise to 1.2 l water. The suspension is stirred for 2.5 h at 0° C., suction filtered and washed with 500 ml of water. The residue is dried overnight at 55° C. under reduced pressure.

Yield: 84.36 g (97.1% of theoretical). m.p.: 120-130° C.

EXAMPLE 5

Diethyl {[4-(3-chloro-4-fluoro-phenylamino)-7-((S)-tetrahydrofuran-3-yloxy)-quinazolin-6-ylcarbamoyl]-methyl}-phosphonate

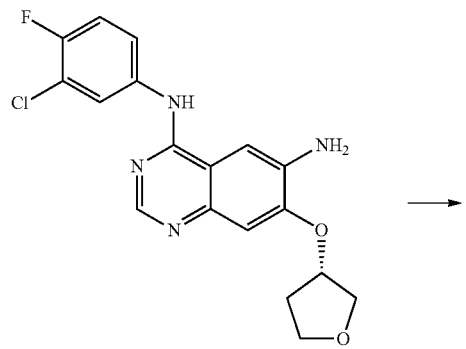

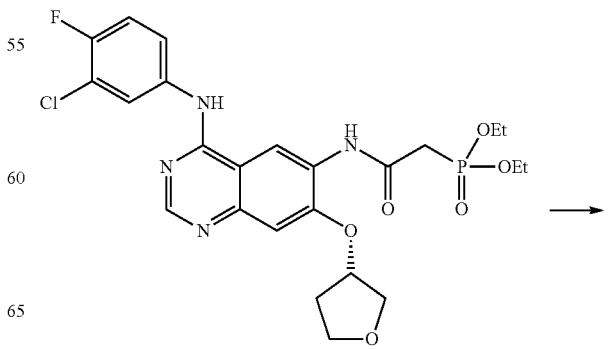

3.58 kg 1,1-carbonyldiimidazole (22.16 mol) are placed in 12.8 l of tetrahydrofuran and combined at 40° C. with 4.52 kg (22.16 mol) diethylphosphonoacetic acid, dissolved in 6.5 l tetrahydrofuran. The mixture is stirred for 30 minutes at 40° C. The solution thus obtained is designated solution A.

6.39 kg (17.05 mol) of $N^4$-(3-chloro-4-fluoro-phenyl)-7-(tetrahydrofuran-3-yloxy)quinazoline-4,6-diamine are placed in 26.5 l tetrahydrofuran and combined at 40° C. with solution A and stirred for 2 hours at 30° C. 64 l of tert.-butylmethylether are added to the suspension and after cooling to 20° C. the precipitate is removed by centrifuging. It is washed with a mixture of 16 l tetrahydrofuran and 16 l tert.-butylmethylether and then with 32 l water and dried at 50° C.

Yield: 6.58 kg (69.8%) white crystals. Content: HPLC 99.1 Fl %

EXAMPLE 6

Dimethylaminoacetaldehyde-Hydrogen Sulphite Adduct 40 g of dimethylaminoacetaldehyde diethylacetal are heated to 40° C. in a mixture of 48 g conc. hydrochloric acid and 20 ml of water for 3 h. Then a solution of 42.4 g sodium pyrosulphite in 72 ml of water (sodium hydrogen sulphite solution) is added dropwise and the mixture is stirred for 1 h. 200 ml of ethanol are added and then the mixture is stirred for 2 h at 0° C. The suspension is suction filtered, washed with 160 ml of ethanol and dried at 45° C. in vacuo.

Yield: 42.5 g (89.6% of theoretical) decomp.: from 180° C.

EXAMPLE 7

(E)-4-Dimethylamino-but-2-enoic acid-[4-(3-chloro-4-fluoro-phenylamino)-7-((S)-tetrahydrofuran-3-yloxy)-quinazolin-6-yl]-amide -continued

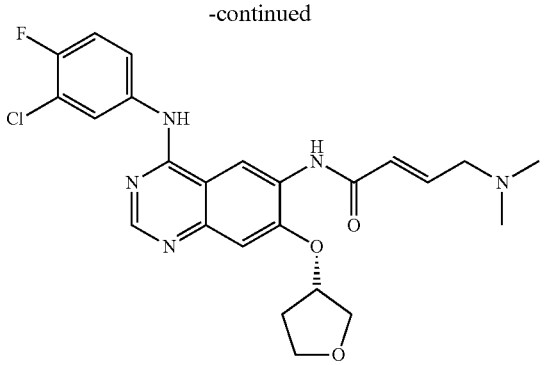

10 g of diethyl {[4-(3-chloro-4-fluoro-phenylamino)-7-((S)-tetrahydrofuran-3-yloxy)-quinazolin-6-ylcarbamoyl]-methyl}-phosphonate and 0.8 g lithium chloride are suspended in 60 ml of ethanol and cooled to −5° C. 11 g of 45% potassium hydroxide solution is added dropwise first of all and then 4.8 g dimethylaminoacetaldehyde-hydrogen sulphite adduct in 48 ml of water is added. The reaction solution is stirred for 1 h and then 60 ml of water are added. The suspension is suction filtered, washed with 40 ml of water and dried in vacuo at 45° C.

Yield: 8 g (91% of theoretical) m.p.: 100-102° C.

The invention claimed is:

1. A compound of the formula

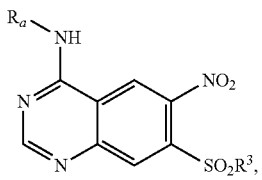

(XIII)

wherein
$R_a$ denotes a benzyl, 1-phenylethyl or 3-chloro-4-fluorophenyl group and
$R^3$ denotes a $C_{1-4}$-alkyl group wherein the hydrogen atoms may be wholly or partly replaced by fluorine atoms, or a phenyl group optionally substituted by one to three substituents selected from $C_{1-3}$-alkyl groups, halogen atoms, cyano or nitro groups, wherein the substituents may be identical or different.

2. A compound of formula (XIII) according to claim 1, wherein $R^3$ denotes the p-toluenesulphonyl, p-bromo-benzenesulphonyl, phenyl, p-nitro-benzenesulphonyl, methylsulphonyl, trifluoromethylsulphonyl, nonafluorobutylsulphonyl or 2,2,2-trifluoroethanesulphonyl group.

3. A compound of formula (XIII) according to claim 1, wherein if $R^3$ denotes a phenyl group, it is optionally substituted by one to three substituents selected from $C_{1-3}$-alkyl groups, fluorine, chlorine, bromine, cyano or nitro groups, wherein the substituents may be identical or different.

4. A compound of formula (XIII) according to claim 1 selected from among:
(1) 4-(3-chloro-4-fluoro-phenylamino)-7-(4-methyl-phenylsulphonyl-)-6-nitro-quinazoline,
(2) 4-(3-chloro-4-fluoro-phenylamino)-7-(4-bromo-phenylsulphonyl)-6-nitro-quinazoline,
(3) 4-(3-chloro-4-fluoro-phenylamino)-7-(phenylsulphonyl)-6-nitro-quinazoline,
(4) 4-(3-chloro-4-fluoro-phenylamino)-7-(4-nitro-phenylsulphonyl)-6-nitro-quinazoline,
(5) 4-(3-chloro-4-fluoro-phenylamino)-7-(methylsulphonyl)-6-nitro-quinazoline,
(6) 4-(3-chloro-4-fluoro-phenylamino)-7-(trifluoromethylsulphonyl)-6-nitro-quinazoline,
(7) 4-(3-chloro-4-fluoro-phenylamino)-7-(nonafluorobutylsulphonyl)-6-nitro-quinazoline,
(8) 4-(3-chloro-4-fluoro-phenylamino)-7-(2,2,2-trifluoroethanesulphonyl)-6-nitro-quinazoline
(9) 4-(benzylamino)-7-(4-methyl-phenylsulphonyl-)-6-nitro-quinazoline,
(10) 4-(benzylamino)-7-(4-bromo-phenylsulphonyl)-6-nitro-quinazoline,
(11) 4-(benzylamino)-7-(phenylsulphonyl)-6-nitro-quinazoline,
(12) 4-(benzylamino)-7-(4-nitro-phenylsulphonyl)-6-nitro-quinazoline,
(13) 4-(benzylamino)-7-(methylsulphonyl)-6-nitro-quinazoline,
(14) 4-(benzylamino)-7-(trifluoromethylsulphonyl)-6-nitro-quinazoline,
(15) 4-(benzylamino)-7-(nonafluorobutylsulphonyl)-6-nitro-quinazoline,
(16) 4-(benzylamino)-7-(2,2,2-trifluoroethanesulphonyl)-6-nitro-quinazoline,
(17) 4-(1-phenylethylamino)-7-(4-methyl-phenylsulphonyl-)-6-nitro-quinazoline,
(18) 4-(1-phenylethylamino)-7-(4-bromo-phenylsulphonyl)-6-nitro-quinazoline,
(19) 4-(1-phenylethylamino)-7-(phenylsulphonyl)-6-nitro-quinazoline,
(20) 4-(1-phenylethylamino)-7-(4-nitro-phenylsulphonyl)-6-nitro-quinazoline,
(21) 4-(1-phenylethylamino)-7-(methylsulphonyl)-6-nitro-quinazoline,
(22) 4-(1-phenylethylamino)-7-(trifluoromethylsulphonyl)-6-nitro-quinazoline,
(23) 4-(1-phenylethylamino)-7-(nonafluorobutylsulphonyl)-6-nitro-quinazoline and
(24) 4-(1-phenylethylamino)-7-(2,2,2-trifluoroethanesulphonyl)-6-nitro-quinazoline.

* * * * *